United States Patent
Richter (10) Patent No.: US 7,998,193 B2
(45) Date of Patent: *Aug. 16, 2011

(54) STENT WITH VARIABLE FEATURES TO OPTIMIZE SUPPORT AND METHOD OF MAKING SUCH STENT

(75) Inventor: Jacob Richter, Arsuf (IL)

(73) Assignee: Medinol Ltd., Tel Aviv (IL)

( * ) Notice: Subject to any disclaimer, the term of this patent is extended or adjusted under 35 U.S.C. 154(b) by 0 days.

This patent is subject to a terminal disclaimer.

(21) Appl. No.: 12/776,518

(22) Filed: May 10, 2010

(65) Prior Publication Data

US 2010/0280593 A1 Nov. 4, 2010

Related U.S. Application Data

(60) Division of application No. 12/170,350, filed on Oct. 2, 2008, now Pat. No. 7,976,576, which is a continuation of application No. 11/373,007, filed on Mar. 9, 2006, now Pat. No. 7,534,257, which is a continuation of application No. 09/599,158, filed on Jun. 21, 2000, now Pat. No. 7,044,963, which is a continuation of application No. 09/040,145, filed on Mar. 17, 1998, now Pat. No. 6,676,697, which is a division of application No. 08/716,039, filed on Sep. 19, 1996, now Pat. No. 5,807,404.

(51) Int. Cl.
*A61F 2/06* (2006.01)
*A61F 2/90* (2006.01)

(52) U.S. Cl. ...................... 623/1.15; 623/1.16; 623/1.17; 623/1.18

(58) Field of Classification Search ......... 623/1.15–1.18
See application file for complete search history.

(56) References Cited

U.S. PATENT DOCUMENTS

| | | | |
|---|---|---|---|
| 5,102,417 | A | 4/1992 | Palmaz |
| 5,135,536 | A | 8/1992 | Hillstead |
| 5,344,426 | A | 9/1994 | Lau et al. |
| 5,354,308 | A | 10/1994 | Simon et al. |

(Continued)

FOREIGN PATENT DOCUMENTS

CA 2252591 4/1996

(Continued)

OTHER PUBLICATIONS

European Search Report Dated Oct. 7, 2009, from related application No. EP 07713084.7, 7 pages.

(Continued)

*Primary Examiner* — David H Willse
*Assistant Examiner* — Javier Blanco
(74) *Attorney, Agent, or Firm* — Cadwalader, Wickersham & Taft LLP (57) ABSTRACT

An intravascular stent especially suited for implanting in curved arterial portions or ostial regions. The stent can include an end region which is fabricated to have a greater radial strength than the remaining axial length of the stent. Such a stent is particularly suited for use in ostial regions, which require greater support near the end of the stent. The stent alternatively can include sections adjacent the end of the stent with greater bending flexibility than the remaining axial length of the stent. Such a stent is particularly suited for use in curved arteries. The stent can also be constructed with an end that has greater radial strength and sections adjacent the end with greater bending flexibility. Such a stent prevents flaring of the stent end during insertion.

6 Claims, 7 Drawing Sheets

U.S. PATENT DOCUMENTS

| | | | |
|---|---|---|---|
| 5,383,892 | A | 1/1995 | Cardon et al. |
| 5,395,390 | A | 3/1995 | Simon et al. |
| 5,449,373 | A | 9/1995 | Pinchasik et al. |
| 5,496,365 | A | 3/1996 | Sgro |
| 5,514,154 | A | 5/1996 | Lau et al. |
| 5,562,697 | A | 10/1996 | Christiansen |
| 5,575,818 | A | 11/1996 | Pinchuk |
| 5,591,197 | A | 1/1997 | Orth et al. |
| 5,716,393 | A | 2/1998 | Lindenberg et al. |
| 5,733,303 | A | 3/1998 | Israel et al. |
| 5,776,161 | A | 7/1998 | Globerman |
| 5,776,183 | A | 7/1998 | Kanesaka et al. |
| 5,800,526 | A | 9/1998 | Anderson et al. |
| 5,807,404 | A | 9/1998 | Richter |
| 5,843,117 | A | 12/1998 | Alt et al. |
| 5,902,317 | A | 5/1999 | Kleshinski et al. |
| 5,913,895 | A | 6/1999 | Burpee et al. |
| 5,922,021 | A | 7/1999 | Jang |
| 5,954,743 | A | 9/1999 | Jang |
| 6,027,526 | A | 2/2000 | Limon et al. |
| 6,039,756 | A | 3/2000 | Jang |
| 6,348,065 | B1 | 2/2002 | Brown et al. |
| 6,375,677 | B1 | 4/2002 | Penn et al. |
| 6,416,539 | B1 | 7/2002 | Hassdenteufel |
| 6,676,697 | B1 | 1/2004 | Richter |
| 7,044,963 | B1 | 5/2006 | Richter |
| 7,534,257 | B2 | 5/2009 | Richter |
| 2001/0044649 | A1 | 11/2001 | Vallana et al. |
| 2002/0007212 | A1 | 1/2002 | Brown et al. |
| 2002/0065549 | A1 | 5/2002 | White et al. |
| 2004/0088040 | A1 | 5/2004 | Mangiardi |
| 2004/0243216 | A1 | 12/2004 | Gregorich |
| 2006/0173531 | A1 | 8/2006 | Richter |
| 2009/0024206 | A1 | 1/2009 | Richter |

FOREIGN PATENT DOCUMENTS

| | | |
|---|---|---|
| CA | 2 214 627 A1 | 9/1998 |
| DE | 4418336 A1 | 11/1995 |
| DE | 29608037 U1 | 7/1996 |
| DE | 69208026 | 9/1996 |
| EP | 0541443 | 5/1993 |
| EP | 0669114 | 8/1995 |
| EP | 0335341 | 7/1996 |
| EP | 0732088 A2 | 9/1996 |
| EP | 0732089 | 9/1996 |
| EP | 0790041 A2 | 8/1997 |
| EP | 0800801 | 10/1997 |
| EP | 1 790 314 A | 5/2007 |
| NO | 19970289 A1 | 3/1997 |
| SU | 1237201 | 6/1986 |
| SU | 1768154 | 10/1992 |
| WO | 92/06734 | 4/1992 |
| WO | 92/16166 | 10/1992 |
| WO | 95/31945 | 11/1995 |
| WO | 95/32688 | 12/1995 |
| WO | 95/32757 | 12/1995 |
| WO | 96/03092 | 2/1996 |
| WO | 96/26689 | 8/1996 |
| WO | 97/40781 | 11/1997 |
| WO | WO 98/40035 A | 9/1998 |
| WO | 03/082154 A2 | 10/2003 |
| WO | WO 2006/047679 A1 | 5/2006 |

OTHER PUBLICATIONS

Office Actions, Responses to Office Actions and Notice of Allowance of related U.S. Appl. No. 08/716,039, issued as U.S. Patent No. 5,807,404: Notice of Allowance dated Dec. 9, 1997; Response to Non-Final Office Action dated Sep. 18, 1997; and Non-Final Office Action dated Mar. 18, 1997.

Office Actions, Responses to Office Actions and Notice of Allowance of related U.S. Appl. No. 09/040,145, issued as U.S. Patent No. 6,676,697: Notice of Allowance dated Aug. 19, 2003; Amendment and Response to Final Office Action dated Jul. 14, 2003; Final Office Action dated Feb. 21, 2003; Response to Non-Final Office Action dated Oct. 24, 2001; Non-Final Office Action dated Sep. 24, 2001; Supplemental Response dated Jun. 21, 2000; Response to Non-Final Office Action dated May 30, 2000; and Non-Final Office Action mailed Feb. 2, 2000.

Office Actions, Responses to Office Actions and Notice of Allowance of related U.S. Appl. No. 09/599,158, issued as U.S. Patent No. 7,044,963: Notice of Allowance dated Dec. 20, 2005; Advisory Action dated Sep. 22, 2005; Amendment and Response to Final Office Action dated Sep. 6, 2005; Final Office Action dated Jun. 6, 2005; Amendment and Response to Non-Final Office Action dated Mar. 15, 2005; Non-Final Office Action dated Dec. 15, 2004; Amendment and Response to Non-Final Office Action dated Sep. 27, 2004; Non-Final Office Acton dated Jun. 21, 2004; Amendment and Response to Final Office Action dated Mar. 3, 2004; Final Office Action dated Aug. 27, 2003; Amendment and Response to Non-Final Office Action dated Jun. 12, 2003; Non-Final Office Action dated Mar. 12, 2003; Amendment and Response to Non-Final Office Action dated Dec. 16, 2002; Non-Final Office Action dated Aug. 15, 2002; and Non-Final Office Action dated Feb. 5, 2002.

Office Actions, Responses to Office Actions of related U.S. Appl. No. 11/366,365: Final Rejection dated May 7, 2010; Amendment and Response to Non-Final Office Action dated Feb. 16, 2010; and Non-Final Rejection dated Nov. 16, 2009.

Office Actions, Responses to Office Actions and Notice of Allowance of related U.S. Appl. No. 11/373,007, issued as U.S. Patent No. 7,534,258: Notice of Allowance and Examiner's Interview Summary dated Jan. 13, 2009; Amendment and Response to Non-Final Rejection & Terminal Disclaimer dated Jul. 17, 2008; Informal or Non-Responsive Amendment dated Jun. 20, 2008; Amendment and Response to Non-Final Office & Terminal Disclaimer Action dated Mar. 14, 2008; Non-Final Office Action dated Nov. 16, 2007; Response to Non-Final Office Action dated Aug. 11, 2007; Non-Final Office Action dated Jul. 11, 2007; Amendment and response to Non-Final Office Action and Extension of Time dated May 16, 2007; and Non-Final Office Action/Election Requirement dated Mar. 23, 2007.

European Search Report Dated Dec. 29, 1997, from related application No. EP 97113109.9, published as EP 0 830 853, 3 pages.

International Search Report and Written Opinion dated Mar. 20, 2008 of related application No. PCT/IB07/00482, published as WO 07/099439, 7 pages.

Norwegian Search Report dated Apr. 15, 1999 from related application No. NO 19973878, granted as NO 313907, 1 page.

Austrian Service Search Report and Written Opinion dated Apr. 14, 2000, from related application No. SG 9702598-5, granted as SG 90023, 6 pages.

STENT WITH VARIABLE FEATURES TO OPTIMIZE SUPPORT AND METHOD OF MAKING SUCH STENT

CROSS-REFERENCE TO RELATED APPLICATIONS

This application is a divisional of application Ser. No. 12/170,350, filed Oct. 2, 2008, now U.S. Pat. No. 7,976,576 which is a continuation of application Ser. No. 11/373,007, filed Mar. 9, 2006 (now U.S. Pat. No. 7,534,257), which is a continuation of application Ser. No. 09/599,158 filed Jun. 21, 2000 (now U.S. Pat. No. 7,044,963), which is a continuation of application Ser. No. 09/040,145 filed Mar. 17, 1998 (now U.S. Pat. No. 6,676,697), which is a division of application Ser. No. 08/716,039, filed Sep. 19, 1996 (now U.S. Pat. No. 5,807,404).

FIELD OF THE INVENTION

The present invention relates generally to stents for implanting into a living body. In particular, the present invention relates to intraluminal stents especially suited for implanting in a variety of lumens having variable characteristics, such as variable curvature, side branching, variable diameter, variable wall compliance or "end effects" of either the lumen, as found, e.g., in ostia, or the stent as the parameters may change at its ends.

BACKGROUND OF THE INVENTION

It is well known to use a stent to expand and impart support to different bodily conduits, such as blood vessels, by expanding a tube-like structure inside the vessel requiring support against collapse or closure. U.S. Pat. No. 5,449,373 shows a stent preferably used for vascular implantation as part of a balloon angioplasty procedure. The stent of U.S. Pat. No. 5,449,373 may be delivered through, or implanted in, a curved vessel. One shortcoming of conventional stents is that they may have deficiencies due to "end effects" where the ends of the stent tend to "flare out" during insertion or after expansion or have a decreased radial force at the end. Still another shortcoming of conventional stents is they do not have different characteristics, (e.g., flexibility and rigidity), to accommodate any changing characteristics of the section of the lumen requiring different stent characteristics.

SUMMARY OF THE INVENTION

The present invention provides for various embodiments of an intraluminal stent which includes varied or different mechanical properties along the axial length of the stent in order to improve stent end effects, or to accommodate variable vessel features. As a result, the various embodiments of the present invention allow for variable properties such as flexibility or radial support between axial regions of the stent. These varied properties can be accomplished in a number of different ways, including decreasing or increasing the thickness or width of elements of one or more of the sections relative to other sections and/or increasing or decreasing the axial length of one or more of the sections and/or changing the cell shape and size and/or changing material properties (e.g., strength, elasticity, etc.) of the material in one section relative to other sections.

The various embodiments of the stents of the present invention may be adapted to provide more flexibility at the ends to allow the stent to accommodate the curvature of a vessel in which the stent is implanted. The degree of flexibility and the distance from the end of the stent to which the extra flexibility is imparted may be varied as specific applications dictate. This flexibility at the ends reduces the chance of a potential trauma point being created in the vessel by the stent tip pressing on the wall outside of the curve if the stent is not flexible enough along its longitudinal axis. In one embodiment of the present invention, flexibility of the stent ends is increased by reducing the gauge of the material used in a section or sections at the stent ends. In another embodiment the flexibility of the stent ends is increased by changing the dimensions of a section or sections at the stent ends. In yet another embodiment of the invention, the flexibility of the stent ends is increased by changing both the dimensions and the gauge of the material used in a section or sections at the stent ends.

The various embodiments of the stents of the present invention may also be adapted to insure increased radial strength at the ends. Radial strength is the resistance of a section of the stent, in an expanded state, to radial contraction. Increasing the radial strength of a stent at the ends is particularly advantageous for stents supporting ostia. Because lesions at an ostium tend to be more calcified or hardened, and therefore require more support, the section of the stent supporting the ostium must be relatively strong. It is also the case that a stent with uniform characteristics has a decreased radial force at the end due to the "end effect" whereby the last row has no support on one side. In one embodiment of the present invention, the strength of the stent at the end supporting, e.g., the ostium, is increased by reducing the length of some sections at the stent end.

The various embodiments of the stent of the present invention also reduce the chance of "flare" at the end of the stent while the stent is being fed into a vessel. During insertion of the catheter delivery system into a curved vessel, the delivery system, including the stent crimped on it, bend along the curvature of the vessel. This bending of the stent can cause a "flaring out" of the leading edge of the stent. This flaring could cause the stent to catch on the surface of the vessel which could result in trauma to the vessel, could inhibit further insertion and proper positioning in the target area, and could cause plaque to break off, which could embolize and clog the vessel. In one embodiment of the present invention, flare is minimized by making the section at the stent end stronger by reducing its length, and by making sections adjacent to the stent end more flexible by reducing their widths, thus, decreasing the bending strength of those sections. Bending strength is the resistance of a section of the stent to axial bending. As a result, the end of the stent remains tightly crimped on the balloon, and the bending moment is taken up by the deformation of the more flexible sections. Upon expansion, the reduced bending strength allows the end of the stent to curve and fit better the curvature of the vessel, thereby, reducing the pressure of the tip of the stent on the internal wall of the vessel being treated.

It is an object of this invention to provide a stent which does not have sharp points or protrusions at its end concentrating pressure on the vessel's wall upon expansion of the stent in a curved portion of a vessel.

It is another object of this invention to provide a stent having a radial force at its distal end that is greater than the radial force in the portion of the stent proximal to the distal end.

It is yet another object of this invention to provide an expandable stent, comprising: a plurality of interconnected flexible cells defining a stent having a proximal end and a distal end and a longitudinal axis, the cells arranged in a plurality of interconnected flexible rows disposed along the longitudinal axis of the stent with a distal row disposed at the distal end of the stent and a proximal row disposed at the proximal end of the stent, wherein the cells disposed in the distal row of the stent are adapted to exert greater radial force and are further adapted to be more flexible than the cells disposed in the rows disposed between the distal row and the proximal end of the stent.

It is still another object of this invention to provide an expandable stent, comprising: a plurality of interconnected flexible cells defining a stent having a proximal end and a distal end and a longitudinal axis, the cells arranged in a plurality of interconnected flexible rows disposed along the longitudinal axis of the stent with a distal row disposed at the distal end of said stent and a proximal row disposed at the proximal end of the stent, wherein the cells in the distal row of the stent and the cells disposed in the proximal row of the stent are adapted to exert greater radial force and are further adapted to be more flexible than the cells disposed in the rows disposed between the distal row and the proximal row.

It is another object of this invention to provide an expandable stent, comprising: a) a plurality of interconnected flexible cells defining a stent having a proximal end and a distal end and a longitudinal axis, the cells arranged in a plurality of interconnected flexible rows disposed the longitudinal axis of the stent with a distal row disposed at the distal end of the stent and a proximal row disposed at the proximal end of the stent, each of the flexible cells comprising a first member, a second member, a third member, and a fourth member, b) a first C-shaped loop disposed between the first member and the third member; c) a second C-shaped loop disposed between the second member and the fourth member; d) a first flexible connector disposed between the first member and the second member; and e) a second flexible connector disposed between the third member and the fourth member, wherein the cells of the distal row are provided with first and third members that are shorter than the second and fourth members in the distal row, and wherein the distal row is provided with first and second flexible connectors that are more flexible than the flexible connectors in the cells in the other rows of the stent.

It is yet another object of this invention to provide an expandable stent, comprising: a) a plurality of interconnected flexible cells defining a longitudinal stent having a proximal end and a distal end and a longitudinal axis, the cells arranged in a plurality of interconnected flexible rows disposed along the longitudinal axis of the stent with a distal row disposed at the distal end of the stent and a proximal row disposed at the proximal end of the stent, each of the flexible cells comprising a first member, a second member, a third member, and a fourth member; b) a first C-shaped loop disposed between the first member and the third member; c) a second C-shaped loop disposed between the second member and the fourth member; d) a first flexible connector disposed between the first member and the second member; and e) a second flexible connector disposed between the third member and the fourth member, wherein the cells of the distal row are provided with first and third members that are shorter than the second and fourth members in the distal row, and wherein the distal row, and the row proximal to the distal row, are provided with first and second flexible connectors that are more flexible than the flexible connectors in the other rows of the stent.

It is a further aspect of this invention to provide an expandable stent comprising: a) a plurality of flexible cells defining a stent having a proximal end and a distal end and a longitudinal axis, the cells arranged in a plurality of flexible rows along the longitudinal axis with a distal row disposed at the distal end of the stent and a proximal row disposed at the proximal end of the stent, each of the flexible cells comprising a first member, a second member, a third member, and a fourth member; b) a first C-shaped loop disposed between the first member and the third member; c) a second C-shaped loop disposed between the second member and the fourth member; d) a first flexible connector disposed between the first member and the second member; and e) a second flexible connector disposed between the third member and the fourth member, wherein the cells of the distal row are provided with first and third members that are shorter than the second and fourth members in the distal row, and wherein the cells of the proximal row are provided with second and fourth members that are shorter than the first and third members in the proximal row, and wherein the distal row, and the row proximal to the distal row, and the proximal row and the row distal to the proximal row are provided with first and second flexible connectors that are more flexible than the flexible connectors in the other rows of the stent.

It is yet another object of this invention to provide an expandable stent, comprising: a plurality of flexible cells defining a stent having a proximal end and a distal end, the stent provided with means for imparting a radial force at its distal end that is greater than the radial force in the portion of the stent proximal to the distal end.

It is yet a further object of this invention to provide an expandable stent, comprising: a plurality of flexible cells defining a stent having a proximal end and a distal end, the stent provided with means for imparting a radial force at its proximal and distal ends that is greater than the radial force of that portion of the stent disposed between the proximal and distal ends.

It is another object of this invention to provide an expandable stent for treating a lumen having a unique characteristic along a portion of the lumen, comprising: a plurality of interconnected flexible cells, the cells arranged in a plurality of interconnected flexible rows defining a stent having a proximal end and a distal end and a longitudinal axis, wherein at least one of the rows is adapted to accommodate the unique characteristic of that portion of the lumen in contact with the adapted row or rows.

It is yet another object of this invention to provide a single flexible stent with a unibody or one-piece construction which is capable of imparting support to a lumen or vessel along the entire length of the stent and in which portions of the stent are adapted or modified so as to have characteristics, e.g., bending strength or radial strength, that are different than the characteristics or features in the rest of the stent along it's longitudinal axis or about its circumference. The change in stent features will either accommodate non-uniformity in the treated lumen or may create different environmental conditions in different areas in the lumen. Non-uniformity in a treated vessel can be of many different types such as an ostium, change in diameter, change in curvature, non-continuous cross-section such as triangular or square, or non-uniformity in surface nature, etc. To accommodate such non-uniformity, portions of the stent may be adapted to provide changing dimension, flexibility, rigidity, size of cells, shape of cells, and response to pressure as dictated by specific applications. Specific applications may dictate, e.g., a desired higher radial force at one end while the other portions of the stent provide a substantially continuous support to the vessel wall with the gaps in the stent sized small enough to reduce the likelihood of tissue prolapse. Other applications may dictate a desired degree of stiffness in the center to reduce the likelihood of breakage and impart the desired degree of softness at the end to allow for the best fit with the anatomy of the target area. Other applications may dictate that one or more of the rows be provided with cells that are sized larger than the cells in the remaining rows of the stent so as to provide access to a side branch in the lumen, e.g., for introducing a second stent through one of the larger sized cells so as to permit construction of a bifurcated stent within the lumen. Still another application may dictate that one or more of the rows be provided with cells which are adapted or modified so that upon expansion of the stent the portion of the stent defined by the adapted or modified row or rows has a diameter that is either larger or smaller than the remaining portions of the stent to accommodate lumens with non-uniform diameters. One or more rows of cells may also be adapted or modified so as to have varying radial force, or varying longitudinal flexibility, or to correct for a change in properties at the end of the stent.

DETAILED DESCRIPTION OF THE INVENTION

Figure 1:
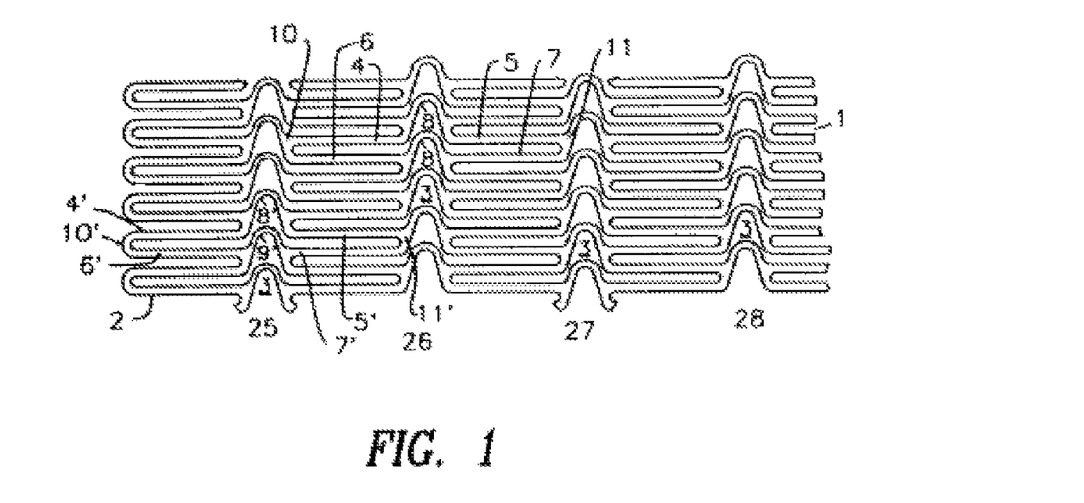
FIG. 1 shows an illustration of the basic pattern of an embodiment of the stent of the present invention, shown in an unexpanded state.

FIG. 1 shows the general configuration of one embodiment of a stent 1 fabricated in accordance with the present invention. The stent 1 may be fabricated of biocompatible materials such as stainless steel 316L, gold, tantalum, nitinol or other materials well known to those skilled in the art as suitable for this purpose. The dimensions and gauge of material utilized may be varied as specific applications dictate. The stents of the present invention generally may be constructed in a manner in accordance with the stent described in U.S. patent application Ser. No. 08/457,354, filed Mar. 31, 1995, now U.S. Pat. No. 5,733,303, the disclosure of which is incorporated herein by reference. In particular, the stents may be formed from a tube, from a flat metal sheet, or from a wire. For example, the stent may be manufactured from flat metal into which a stent pattern is etched. The etched pattern may then be bent to form the tubular stent. Alternatively, the stent may be manufactured by twisting or welding a wire.

Figure 2:
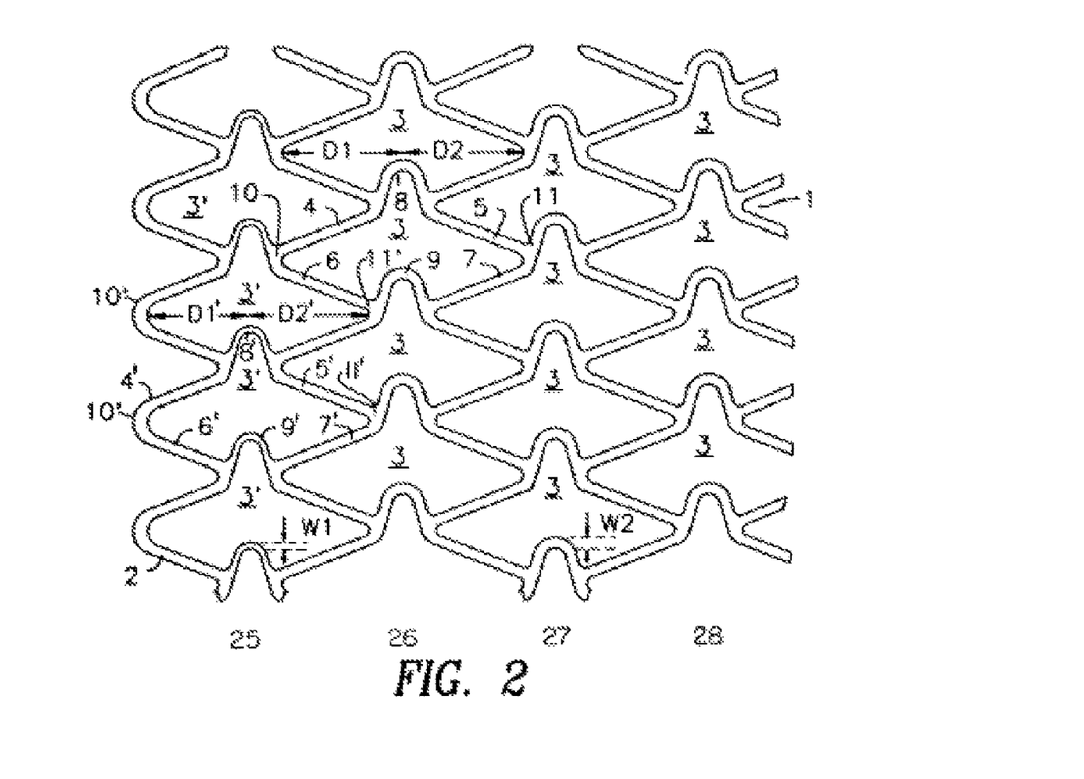
FIG. 2 shows an illustration of the pattern of the stent of FIG. 1, in a partially expanded state.
Figure 11:
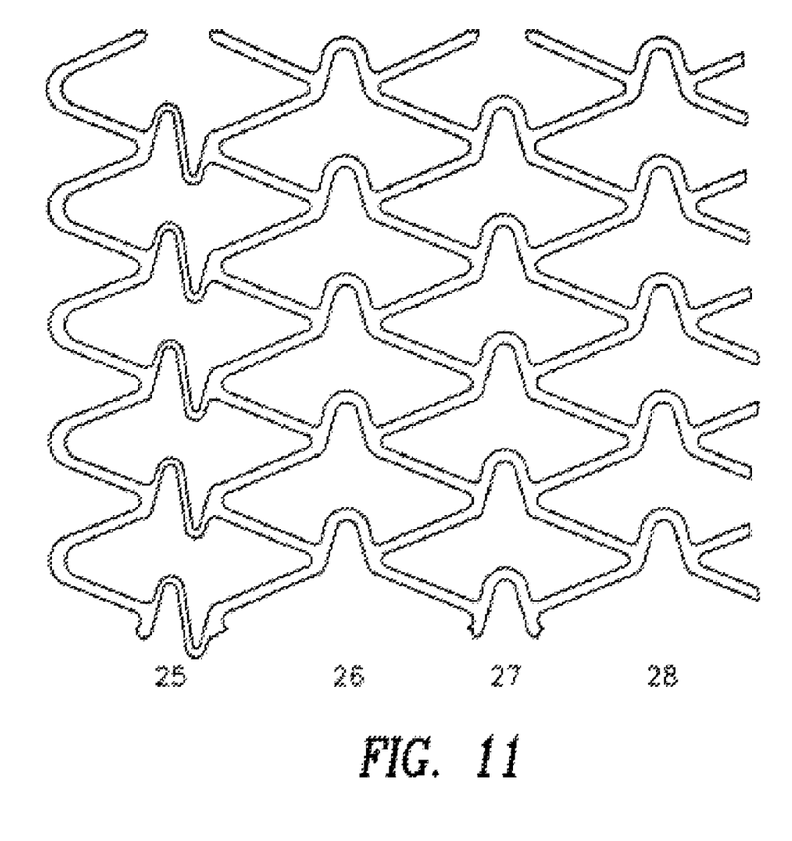
FIG. 11 shows the "S" or "Z" shaped loops constructed in accordance with the invention.

FIG. 1 is a side view of the distal end 2 of stent 1 of the present invention, showing the general pattern of the stent. As shown in FIGS. 1 and 2 the pattern may be described as a plurality of cells 3 and 3'. Each cell 3 is provided with a first member 4, a second member 5, a third member 6, and a fourth member 7. A first C-shaped loop 10 is disposed between the first member 4 and the third member 6 and a second C-shaped loop 11 is disposed between the second member 5 and the fourth member 7. In each of the cells 3, first member 4, second member 5, third member 6, and fourth member 7 are substantially equal. Thus, first C-shaped loop 10 is displaced a distance D1 and second C-shaped loop 11 is displaced a distance D2 from the center of cell 3. In a preferred embodiment, D1 is substantially equal to D2. A first flexible connector 8 is disposed between the first member 4 and the second member 5 and a second flexible connector 9 is disposed between third member 6 and fourth member 7. The flexible connectors 8 and 9 may be made in a variety of shapes, e.g., an "S" or a "Z" shape as shown in FIG. 11. In a preferred embodiment, a "U" shape is utilized as shown in FIGS. 1 to 10.

FIG. 1 shows the pattern of stent 1 in an unexpanded state, i.e., that state in which the stent 1 is first inserted in a particular vessel in which a balloon angioplasty procedure is to be performed, but before balloon inflation. FIG. 2 shows the pattern of stent 1 in a partially expanded state, i.e., that state after the balloon has been expanded, e.g. by a balloon, and the state in which the stent 1 remains in the vessel which it supports. The plurality of interconnected cells 3 and 3' form a plurality of interconnected rows 25, 26, 27, and 28 of cells disposed along the longitudinal axis of the stent 1. FIGS. 1 and 2 show a distal row 25 disposed at the distal end 2, a row 26 adjacent to and proximal to distal row 25, a row 27 adjacent to and proximal to row 26, and a row 28 adjacent to and proximal to row 27. It will be appreciated that the number of rows, and the number of cells per row, and the shape of each cell, may be varied as specific applications require.

As shown in FIGS. 1 and 2, the cells 3' in distal row 25 differ from the cells 3 in rows 26, 27, and 28. The first member 4' and the third member 6' of the cells 3' in row 25 are shorter than the first member 4 and the third member 6 of the cells 3 in rows 26, 27 and 28. In cell 3', first member 4' is substantially equal to third member 6', however, first member 4' and third member 6' are shorter than second member 5' and fourth member 7'. The shorter members 4' and 6' result in a first C-shaped loop 10' that is not disposed as far away from the center of the cell 3' as second C-shaped loop 11'. Thus, first C-shaped loop 10' may be thought of as being "shorter" than second C-shaped loop 11'. As shown in FIG. 2, first C-shaped loop 10' is disposed a distance D1' that is less than the distance D2' that second C-shaped loop 11' is disposed from the center of the cell 3'. In an especially preferred embodiment, D1' is about 15% less than D2'.

FIGS. 1 and 2 also show that the distal row 25 of the stent 1 is provided with a first U-shaped loop 8' and a second U-shaped loop 9' that are more flexible than the first U-shaped loop 8 and second U-shaped loop 9 of cells 3 in rows 26, 27, and 28 of the stent 1. This greater flexibility in the U-shaped loops 8' and 9' may be accomplished in a variety of ways, for example, by utilizing a different material, by treating the material e.g., by utilizing stainless steel annealing to impart selective degrees of hardness to the different portions of the stent. Alternatively, if, e.g., NiTi (Nitinol) is utilized, selected portions of the stent may be selectively thermo-mechanically treated so that portions of the stent, e.g., the U-shaped members, will remain in a martensitic phase while other portions of the stent will be transformed into austenitic phase in this section to yield different properties. Greater flexibility may also be achieved by changing the shape of the "U", for example to a "Z" or an "S" (as shown in FIG. 11), or by reducing the amount of material utilized to make the U-shaped loops 8' and 9'. In the embodiment shown in FIGS. 1 and 2, the U-shaped loops 8' and 9' of row 25 are provided with the same thickness of material as the U-shaped loops 8 and 9 of the cells 3 in rows 26, 27, and 28, however, U-shaped loops 8' and 9' are not as wide. As shown in FIGS. 1 and 2, U-shaped loops 8' and 9' have a width W1 that is less than the width W2 of U-shaped loops 8 and 9 in the cells 3 of rows 26, 27, and 28. In a preferred embodiment, W1 is about 50% narrower than W2. In an especially preferred embodiment, W1 is about 40% narrower than W2.

Figure 3:
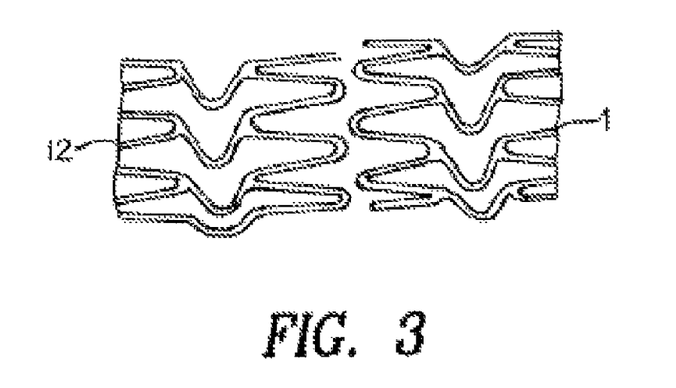
FIG. 3 is a side view showing a conventional stent and a stent manufactured in accordance with one embodiment of the invention.
Figure 4:
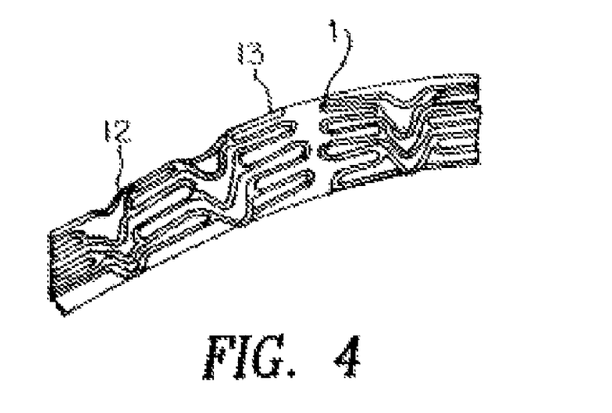
FIG. 4 shows the stents of FIG. 3 crimped on a balloon catheter and bent prior to expansion.
Figure 5:
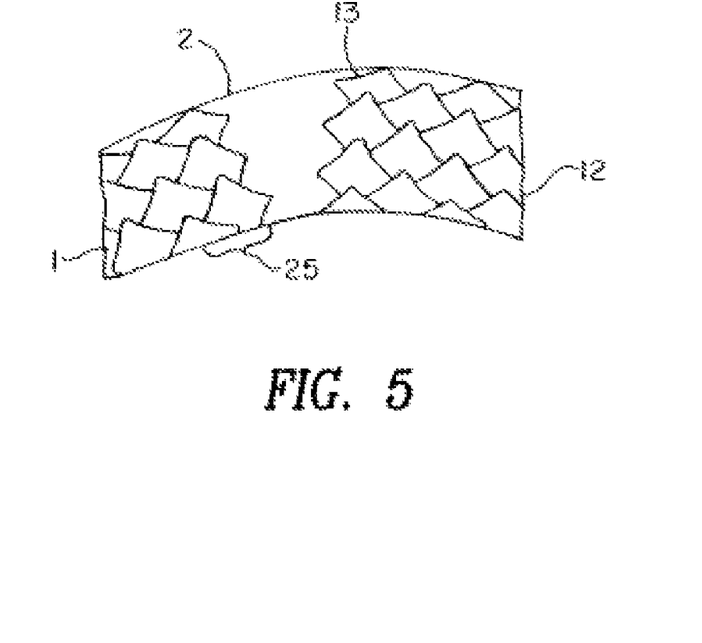
FIG. 5 shows the stents of FIG. 4 after they have been expanded in a curve.

FIG. 3 is a side-by-side comparison of two stent sections and shows a conventional stent 12 compared to the stent 1, shown in FIGS. 1 and 2. FIG. 4 shows stents 1 and 12 shown in FIG. 3 as (hey appear when they are crimped on a balloon and bent as they would be during insertion around a curve in a vessel. As shown in FIG. 4, conventional stent 12 flares at its leading edge 13 in contrast to stent 1 which does not. FIG. 5 shows the stents of FIG. 4 after the stents have been expanded in a curve. The tip of conventional stent 12 produces a protrusion or sharp point 13 which could cause local pressure and possible trauma to the vessel wall. In contrast, the stent 1 constructed in accordance with the invention bends gently at its end 2 without forming a protrusion or sharp point because the deformation of the of U-shaped loops 8' and 9' in distal row 25 make the end 2 softer.

Figure 6:
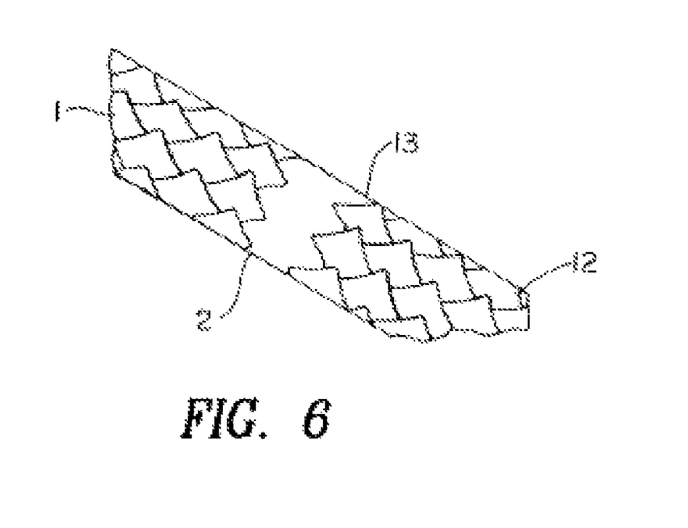
FIG. 6 shows the stents of FIG. 3 partially expanded on a substantially straight balloon catheter.

FIG. 6 shows the stents 1 and 12 of FIG. 3 at partial expansion (before reaching maximum pressure) disposed on a substantially straight catheter. As shown, although the two stents 1 and 12 are subjected to the same outward force, the end 2 of stent 1 is less expanded than the end 13 of conventional stent 12 demonstrating the increased radial force of the end 2 of stent 1 constructed in accordance with the invention. At full pressure the radii of the stents 1 and 12 will be equal, however, the end 2 of stent 1 will have greater radial resistance to collapse than the end 13 of stent 12.

Figure 7:
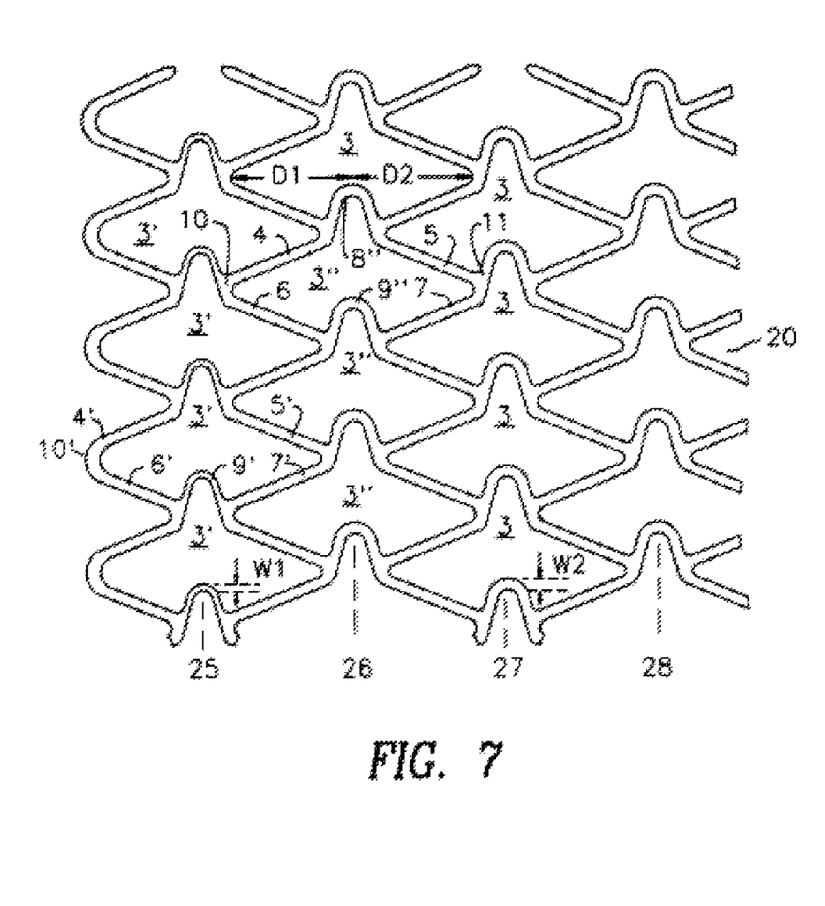
FIG. 7 shows an alternative embodiment of the invention provided with a shortened C-shaped loop and in which two rows of cells are provided with thinner gauge U-shaped loops.

FIG. 7 shows an alternative embodiment of the invention. As shown in FIG. 7, the cells 3' in row 25 are provided with a first member 4' and third member 6' that are shorter than second member 5' and fourth member 7'. The cells 3' in row 25 are provided with a first U-shaped loop 8' and a second U-shaped loop 9' that are thinner than the U-shaped loops 8 and 9 in the cells 3 in rows 27 and 28. The cells 3" in row 26 are provided with first U-shaped loops 8'" and second U-shaped loops 9'" that are narrower than the U-shaped loops 8 and 9 in the cells 3 in rows 27 and 28.

Figure 8:
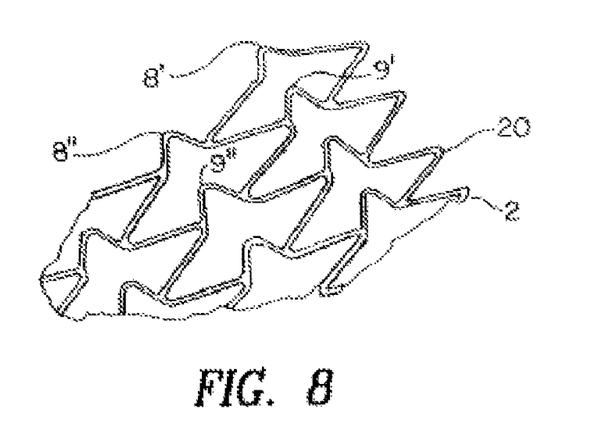
FIG. 8 shows the stent of FIG. 7 partially expanded on a substantially straight balloon catheter.

FIG. 8 shows the stent 20 of FIG. 7 during partial expansion of the stent showing the decreased expansion of row 25 at partial expansion because of the higher radial force of the end 2 of the stent which results from construction with shorter C-shaped loops 10' in row 25, construction with narrower, i.e., more flexible, U-shaped loops 8' and 9' in row 25, and 8'" and 9'" in row 26.

Figure 9:
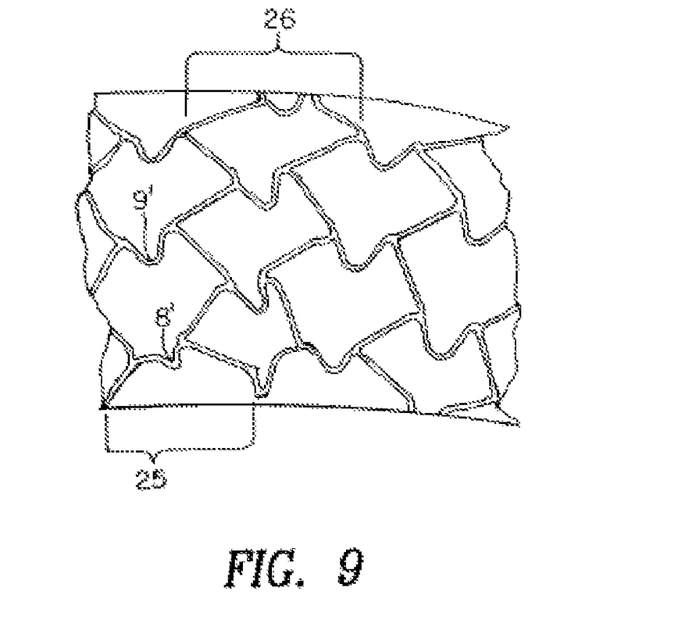
FIG. 9 shows the stent of FIG. 7 after it has been expanded on a curved catheter as it would be when inserted around a bend in a vessel.

FIG. 9 shows the stent 20 of FIGS. 7 and 8 after it has been expanded in a curved vessel and shows the bends of the U-shaped loops 8' and 9' in row 25 and 8'" and 9'" in row 26 which allows the end portion 2 of the stent 20 to more readily conform to the curve of the vessel, creating smooth ends with no sharp points or projections projecting into the vessel wall.

The changes can be made on one side only or on both sides of the stent as specific applications dictate. Additionally, different combinations of embodiments of the invention may be mixed such as using thinner U-shaped loops, longer U-shaped loops or different shaped loops, e.g., "Z" or "S".

Figure 10:
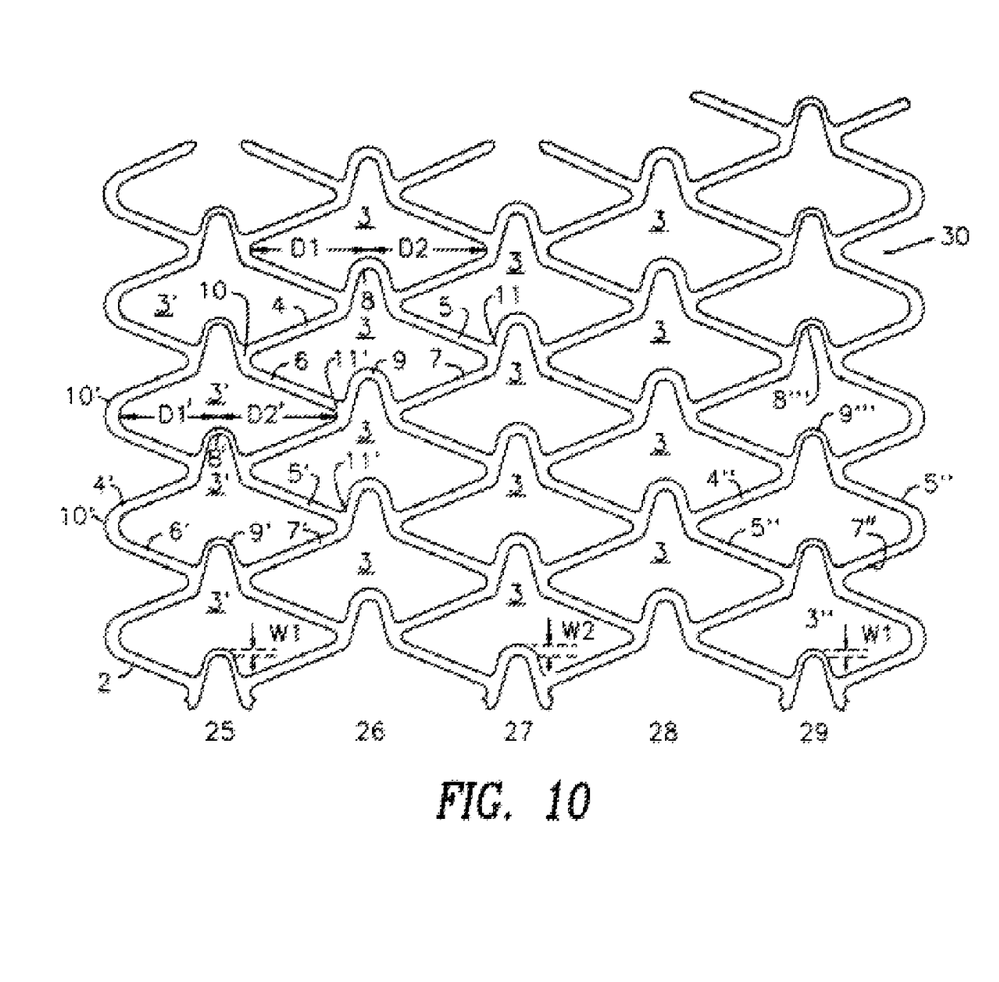
FIG. 10 shows an alternative embodiment of a stent constructed in accordance with the invention.

One example of how this may be achieved is shown in FIG. 10. FIG. 10 shows how the stent shown in FIG. 7 may be modified, if additional flexibility is desired. As shown in FIG. 10, the distal row 25, and the proximal row 29 of stent 30 are provided with first and second U-shaped loops that are more flexible than the U-shaped loops in the other rows of the stent disposed between the distal and proximal rows 25 and 29. In the embodiment of the invention shown in FIG. 10, the distal row 25 is provided with shortened members 4' and 6' and more flexible U-shaped loops 8' and 9', as previously discussed, and the proximal row 29 is provided with shortened second and fourth members 5" and 7" and more flexible U-shaped loops 8'" and 9'". This arrangement imparts greater radial strength and greater flexibility to both ends of the stent.

If even greater flexibility at the ends of the stent is desired, the stent shown in FIG. 10 may be modified by replacing the U-shaped loops in rows 26 and 28 with more flexible loops. Thus, the distal row, the row proximal to the distal row, the proximal row, and the row distal to the proximal row are provided with U-shaped loops that are more flexible than the U-shaped loops in the cells in the remaining rows of the stent.

The present invention contemplates a number of different variations and changes in different properties to achieve other non uniform features such as, but not limited to, cell size, cell shape, radio-opacity, etc. on the above-described preferred embodiments. The specified changes are brought only as an example for the application of the general concept, which is the basis for the present invention that stents with varying mechanical properties between sections along the stent may correct undesired effects at singular points such as stent ends and provide for a better fit to a vessel with properties changing along its axis. It is to be understood that the above description is only of one preferred embodiment, and that the scope of the invention is to be measured by the claims as set forth below.

What is claimed is:

1. An expandable tubular stent, comprising in both expanded and unexpanded form:
   a) a plurality of interconnected flexible cells defining a stent having a proximal end, a central section, a distal end, and a longitudinal axis, the cells arranged in a plurality of interconnected flexible rows of cells disposed along the longitudinal axis of the stent with at least one distal row disposed at the distal end of the stent and at least one proximal row disposed at the proximal end of the stent, each of the flexible cells comprising a first member, a second member, a third member and, a fourth member;
   b) a first C-shaped loop disposed between the first member and the third member;
   c) a second C-shaped loop disposed between the second member and the fourth member;
   d) a first flexible loop connector disposed between the first member and the second member; and
   e) a second flexible loop connector disposed between the third member and the fourth member;
   adjacent rows of cells connected to each other;
   wherein the first and third members of the cells of a distal end row of cells are shorter than the second and fourth members of said cells, wherein said distal end exerts greater radial strength than said central section of the stent.

2. The stent of claim 1, wherein the first and the third members in the cells of the distal end row of cells are about 15% shorter than the second and the fourth members.

3. An expandable tubular stent, comprising in both expanded and unexpanded form:
   a) a plurality of interconnected flexible cells defining a stent having a proximal end, a central section, a distal end, and a longitudinal axis, the cells arranged in a plurality of interconnected flexible rows of cells disposed along the longitudinal axis of the stent with at least one distal row disposed at the distal end of the stent and at least one proximal row disposed at the proximal end of the stent, each of the flexible cells comprising a first member, a second member, a third member and, a fourth member;

b) a first C-shaped loop disposed between the first member and the third member;

c) a second C-shaped loop disposed between the second member and the fourth member;

d) a first flexible loop connector disposed between the first member and the second member; and e) a second flexible loop connector disposed between the third member and the fourth member;

adjacent rows of cells connected to each other;

wherein the second and fourth members of the cells of a proximal end row of cells are shorter than the first and third members of said cells, wherein said proximal end exerts greater radial strength than said central section of the stent.

4. The stent of claim 3, wherein the second and the fourth members in the cells of the proximal end row of cells are about 15% shorter than the first and the third members.

5. An expandable tubular stent, comprising in both expanded and unexpanded form:

a) a plurality of interconnected flexible cells defining a stent having a proximal end, a central section, a distal end, and a longitudinal axis, the cells arranged in a plurality of interconnected flexible rows of cells disposed along the longitudinal axis of the stent with at least one distal row disposed at the distal end of the stent and at least one proximal row disposed at the proximal end of the stent, each of the flexible cells comprising a first member, a second member, a third member and, a fourth member;

b) a first C-shaped loop disposed between the first member and the third member;

c) a second C-shaped loop disposed between the second member and the fourth member;

d) a first flexible loop connector disposed between the first member and the second member; and e) a second flexible loop connector disposed between the third member and the fourth member;

adjacent rows of cells connected to each other;

wherein the first and third members of the cells of a distal end row of cells are shorter than the second and fourth members, and the second and fourth members of the cells of a proximal end row of cells are shorter than the first and third members, wherein said distal end and said proximal end exert greater radial strength than said central section of the stent.

6. The stent of claim 5, wherein the first and the third members in the cells of the distal end row of cells are about 15% shorter than the second and the fourth members, and the second and the fourth members in the cells of the proximal end row of cells are about 15% shorter than the first and the third members.

\* \* \* \* \*